(12) United States Patent
Pouteau et al.

(10) Patent No.: US 8,216,827 B2
(45) Date of Patent: Jul. 10, 2012

(54) DEVICE FOR BIOASSAYS WITH INTEGRATED DETECTOR

(75) Inventors: Patrick Pouteau, Meylan (FR);
Raymond Campagnolo, Grenoble (FR);
Frederic Mallard, Voreppe (FR);
Frederic Ginot, Saint Egreve (FR)

(73) Assignees: Commissariat a l'Energie Atomique, Paris (FR); Biomerieux SA, Marcy l'Etoile (FR)

( * ) Notice: Subject to any disclaimer, the term of this patent is extended or adjusted under 35 U.S.C. 154(b) by 389 days.

(21) Appl. No.: 11/815,147

(22) PCT Filed: Jan. 31, 2006

(86) PCT No.: PCT/FR2006/050080
§ 371 (c)(1),
(2), (4) Date: Jul. 31, 2007

(87) PCT Pub. No.: WO2006/082336
PCT Pub. Date: Aug. 10, 2006

(65) Prior Publication Data
US 2009/0013768 A1 Jan. 15, 2009

(30) Foreign Application Priority Data

Feb. 2, 2005 (FR) .................................. 05 50306

(51) Int. Cl.
*C12M 1/34* (2006.01)
(52) U.S. Cl. ............... 435/288.7; 435/287.2; 435/288.5; 435/7.32; 422/502; 422/82.05; 422/504; 422/509; 422/505; 436/172; 436/525; 436/518

(58) Field of Classification Search ........................ None
See application file for complete search history.

(56) References Cited

U.S. PATENT DOCUMENTS

| 5,653,939 | A | * | 8/1997 | Hollis et al. | 506/3 |
| 5,846,392 | A | | 12/1998 | Knoll | |
| 6,277,629 | B1 | * | 8/2001 | Wolf et al. | 435/288.3 |
| 6,325,977 | B1 | | 12/2001 | Theil | |
| 6,537,801 | B1 | * | 3/2003 | Ida et al. | 435/287.2 |

FOREIGN PATENT DOCUMENTS

| EP | 1 314 472 | 5/2003 |
| FR | 2 824 335 | 11/2002 |
| JP | 7-508831 | 9/1995 |
| JP | 9-510541 | 10/1997 |
| JP | 2001-524329 | 12/2001 |
| JP | 2002-526773 | 8/2002 |

(Continued)

OTHER PUBLICATIONS

A. Troesch, et al., "*Mycobacterium* Species Identification and Rifampin Resistance Testing with High-Density DNA Probe Arrays", Journal of Clinical Microbiology, vol. 37, No. 1, Jan. 1999, pp. 49-55.

(Continued)

*Primary Examiner* — Sally Sakelaris
(74) *Attorney, Agent, or Firm* — Oblon, Spivak, McClelland, Maier & Neustadt, L.L.P.

(57) ABSTRACT

The disclosure relates to a biological analysis device including:
means for circulating a fluid to be analyzed, comprising a fluidic chamber,
optical detection means based on a semiconductor, including a detection front face, a rear face and pads of electrical contacts located on this rear face.

21 Claims, 7 Drawing Sheets

FOREIGN PATENT DOCUMENTS

| | | |
|---|---|---|
| JP | 2002-527254 | 8/2002 |
| JP | 2004-125777 | 4/2004 |
| JP | 2005-24483 | 1/2005 |
| JP | 2008-102135 | 5/2008 |
| WO | WO 2004/042399 | 5/2004 |
| WO | 2004 062801 | 7/2004 |

OTHER PUBLICATIONS

V. Monnot, et al., "Labeling During Cleavage (LDC), A New Labeling Approach for RNA", Nucleosides, Nucleotides & Nucleic Acids, 20(4-7), 2001, pp. 1177-1179.

Stephen P.A. Fodor, et al., "Light-Directed, Spatially Addressable Parallel Chemical Synthesis", Research Article, Feb. 15, 1991, pp. 767-773.

Ann Caviani Pease, et al., "Light-generated oligonucleotide arrays for rapid DNA sequence analysis", Proc. Natl. Acad. Sci. USA, vol. 91, May 1994, pp. 5022-5026.

Robin H. Liu, et al., "Integrated Microfluidic Biochips for Electrochemical Detection of Multiple Bioagents", $8^{th}$ International Conference on Miniaturized Systems for Chemistry and Life Sciences, Sep. 26-30, 2004, 2 pages.

J. F. Kuhmann, et al., "Through Wafer Interconnects and Flip-Chip Bonding: A Toolbox for Advanced Hybrid Technologies for MEMS", Eurosensors XIII, $13^{th}$ European Conference on Solid-State Transducers, 1999, pp. 265-272.

Frédéric Mallard, et al., "Opto-electronic DNA chip: high performance chip reading with an all-electric interface", www.sparksdesigns.co.uk/biopapers04/posters.asp, pp. 1-20, Mar. 15, 2005.

Office Action mailed Feb. 7, 2012, in Japanese Patent Application No. 2007-553665, filed Sep. 28, 2007 (with English-language Translation).

* cited by examiner

DEVICE FOR BIOASSAYS WITH INTEGRATED DETECTOR

TECHNICAL FIELD AND PRIOR ART

The main application field of this invention is that of <<lab-on-chips>>, or integrated analysis devices or IAD (a microelectronic component in which one or several chemical and/or biological reactions are conducted), or biochips (a microelectronic support provided with biological probes) notably used for detecting and characterizing DNA or proteins. In particular it allows an integrated read-out of such devices.

Documents U.S. Pat. Nos. 5,653,939 and 6,325,977 describe the use of CCD (or CMOS) optical sensors as a substrate for making the detection portion of the biochip. The molecules to be analyzed may be marked by a fluorescent or chemiluminescent label.

For other IADs, detection is no longer optical but electrical, from electrons generated by the marker associated with the molecules to be analyzed and which are directly read out by the read-out circuit. For example, reference may be made to the article of Robin H. Liu et al., <<Integrated Microfluidics Biochips for Electrochemical Detection of Multiple Bioagents>>, 8th International Conference on Miniaturized Systems for Chemistry and Life Sciences, Sep. 26-30, 2004, Malmö, Sweden.

FIG. 1 is a view of a standard APS component 2 in CMOS technology. This figure gives a practical example of the useful surfaces on the front face of a detection component 2. By component, is meant the substrate bearing the detection means 54 and the associated integrated processing means. The array of the passivated pixels 54 and the metal pads 42 for resuming electric contacts are shown on the same front face.

The areas 4 grouping the whole of the contact pads 42 take up consequent space on the front face of this component. According to the types of components and their applications, the contact areas may be found again on the four edges of the component, or on three or two of them or even on a side of the component. These reserved areas may be of a width ranging up to 500 μm according to the manufacturing technologies or according to the technologies for resuming electrical contacts.

The positioning of these contacts on the same face of the component as the one bearing the optical detection means 54 and close to the latter poses a certain number of problems:
these contacts consist of metals (gold, platinum, aluminium or amalgam . . . ). These metals are found again at the surface of the component. For integrated detection applications, the manufacturing step following the making of the electrical contacts consists of achieving functionalization of the detection surfaces by performing chemical steps for immobilizing biological probes. Now, most of the chemical functionalization methods include oxidation, reduction steps or steps in an acid phase which are, at one moment or another, aggressive towards metals. Several of these steps alter the nature of these metals, there may even be a complete destruction of the contact.

It is therefore difficult, or even impossible to depassivate the contact pads before functionalization. Now, depassivation before functionalization allows the functionality of the electronic read-out circuit to be tested, a major step for ensuring the quality of an industrial process. Conversely if depassivation is performed after functionalization, it may degrade biological probes because it requires aggressive technological steps, for example etching.

once the components have been functionalized, the electrical contacts should be resumed on another support (a memory film, for example a PCT (polycarbonate bench) 6 or other, see FIGS. 2 and 4). Now, if the whole of the component (including resumption of the contacts) is integrated into the fluidic portion of the integrated analysis device (or IAD), the contacts and their resumptions 7 should be passivated in order to avoid any short-circuit between the different contacts or any alteration of the electrical connections. This may be achieved by passivation resins or polymers 8 (FIG. 2), which generates overthicknesses (several hundreds of microns) in the fluidic portion of the IAD, which perturb fluidic flow. This further provides significant stresses for fluidic closing of the component.

In another configuration, illustrated in FIG. 4, the connection portion 10 of the component is positioned outside the fluidic portion 12. This solution poses problems of a sealed assembly, of lost space for achieving this seal between the sensitive area of the chip and the connection area, of perturbation of the fluidic flow and also of assembling accuracy.

FIG. 3 illustrates another known configuration, in which an optical detection layer 20 on a substrate 22 includes side contacts 24 covered with a conductive adhesive 26 and a passivation resin.

FIG. 5 illustrates another known configuration, in which optical detection means are formed on a substrate 32, side contacts 34 being isolated from the fluidic area, delimited by walls 36.

For all these devices, the problems already mentioned above are posed.

The problem of integrating the fluidic functions required for preparing the biological sample with the detection functions is also posed.

One object of the present invention is to provide a new type of biological analysis device, with optical and/or electrical detection means, with which the fluidic flow of a sample to be analyzed may not be limited or perturbed.

Another object of the present invention is to make a device, the electronic functionality of which may be tested before and/or after functionalization.

PRESENTATION OF THE INVENTION

The invention relates to a biological analysis device including:
means for circulating a fluid to be analyzed, comprising a fluidic chamber,
detection means, based on a semiconductor, or based on semiconducting material or in a semiconducting chip, including a front detection face, intended to be in contact with the fluid to be analyzed in the fluidic chamber, a rear face, and electrical contact pads located on this rear face.

According to the invention, detector(s) are therefore used, for which the electric contact pads are transferred onto the rear face of the chip.

This allows on the front face, only having the detection portion, possibly covered with a passivation layer, for example a silicon nitride or silicon oxide layer.

It is also possible to have on the front face, electronic processing devices at one or more pixels. The outer contact with its components is provided via the contact pads located on the rear face.

Such a use facilitates the steps for manufacturing biological probes on the surface of the component including detection means and improves the possibilities of integration of a detection technology in a IAD, in particular in its microfluidic portion.

According to the invention, technologies of detectors for example of the CMOS or CCD or NMOS or biCMOS type may therefore be used; these detectors may possibly be arranged in an array, with resumption of electric contact on the rear face.

The front face may be functionalized by biological and/or chemical probes.

The detection means may be of the optical type, for example fluorescence detection means, which may possibly include a wavelength filter.

The detection means further are for example, means for detecting bioluminescence or chemiluminescence, which may include biological probes marked with an enzyme capable of emitting a photon, upon contacting a specific molecule contained in the fluid to be analyzed.

According to one alternative, the detection means are electric detection means, for example electrochemical means.

Preferably, the detection means are flush with the fluidic chamber at a flow surface of a fluid.

Sealing means may be provided around the detection means, or in an area in proximity to these detection means, or in an area for inserting detection means into the chamber.

The perimeter of the component and/or the fluidic chamber may advantageously include supporting planes.

A device according to the invention may further include heating means on the rear face side of the detection means, i.e., in contact with, or facing, or integrated to the detection means.

Read-out means, positioned in contact with the pads on the rear face of the detection component, allow the signals to be read out during the use of the device.

Additionally, a memory film may be positioned in contact with the pads on the rear face of the component.

The contact pads are provided and compatible with direct interconnection of the detection means and of an outer reader, for example of the chip card type.

The invention also relates to a use of a device according to the invention for carrying out biological analyses.

SHORT DESCRIPTION OF THE DRAWINGS

Figure 10:
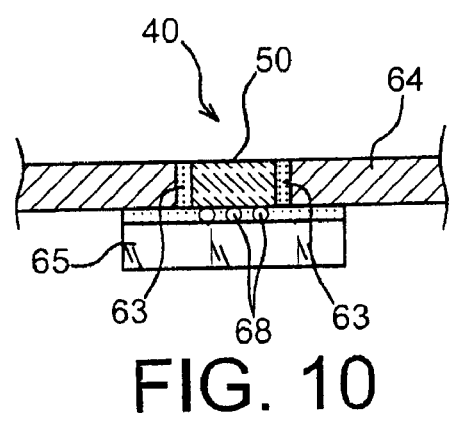
Figure 11:
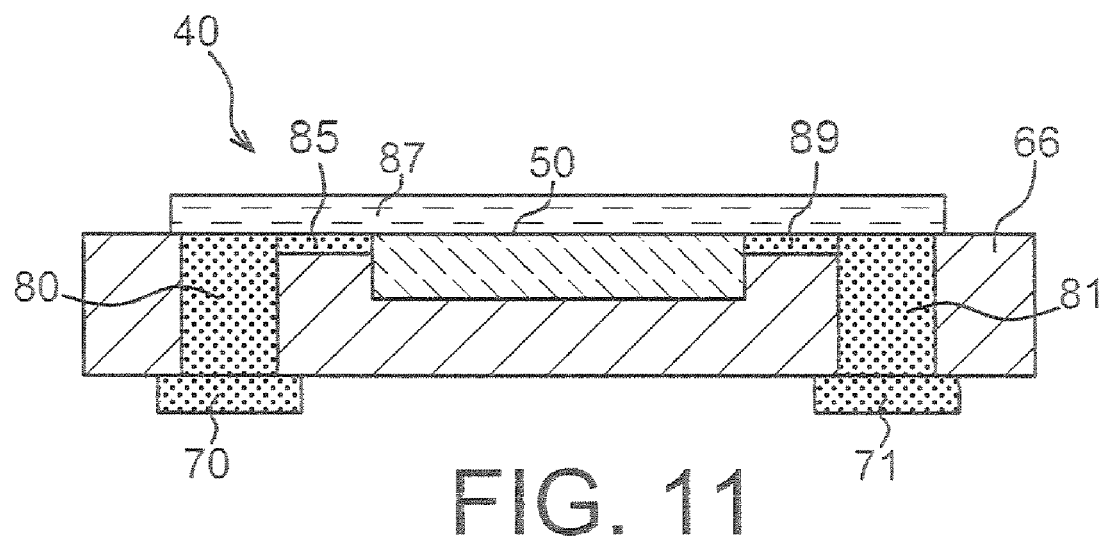
Figure 12:
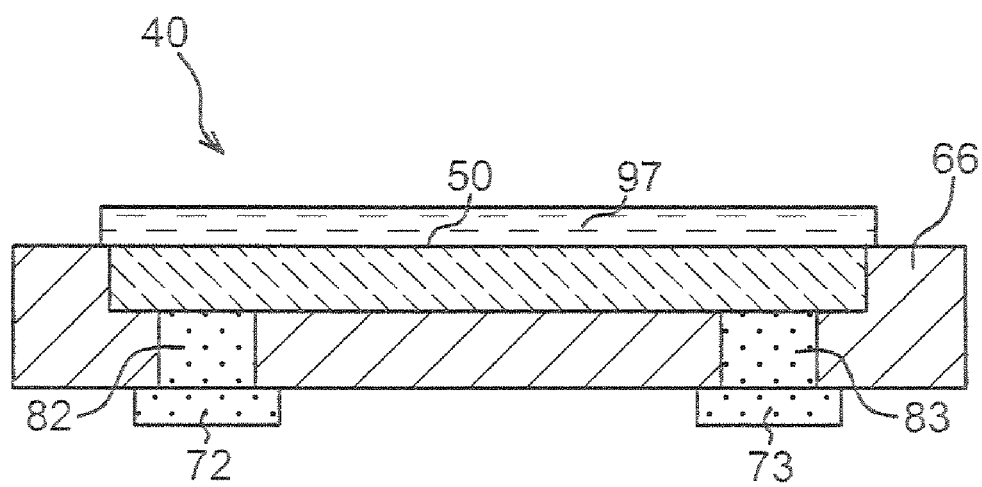
Figure 13:
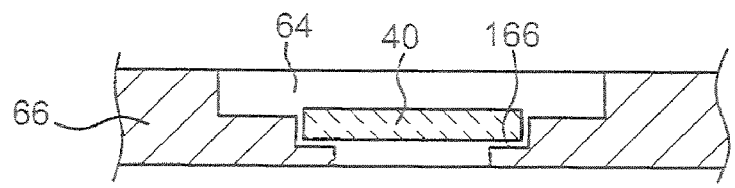
Figure 14:
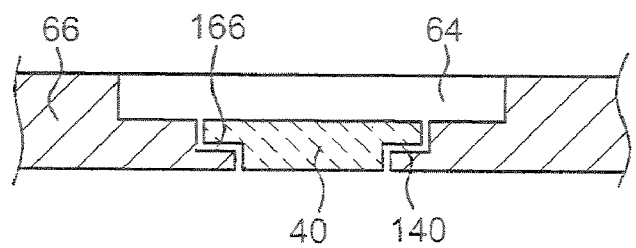
Figure 15:
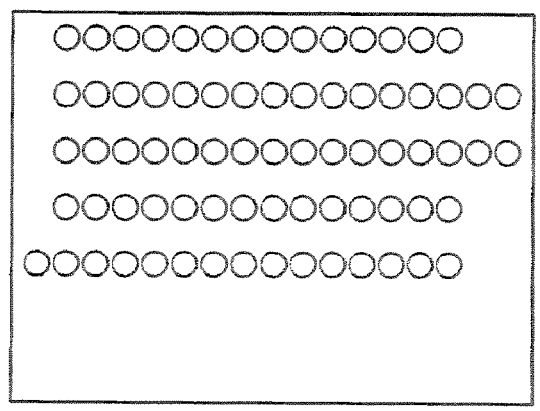
Figure 16A:
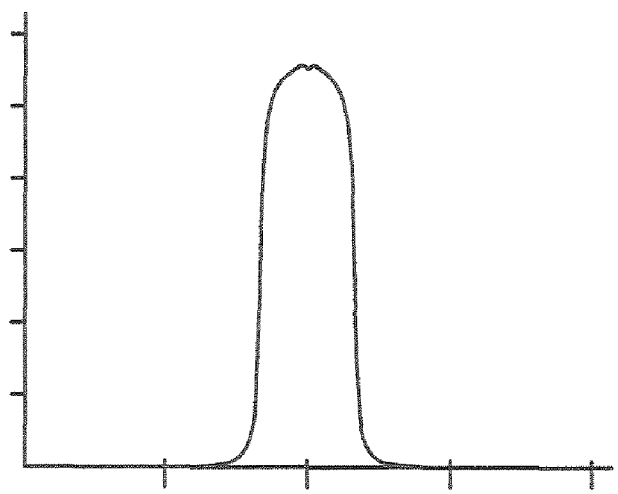
Figure 16B:
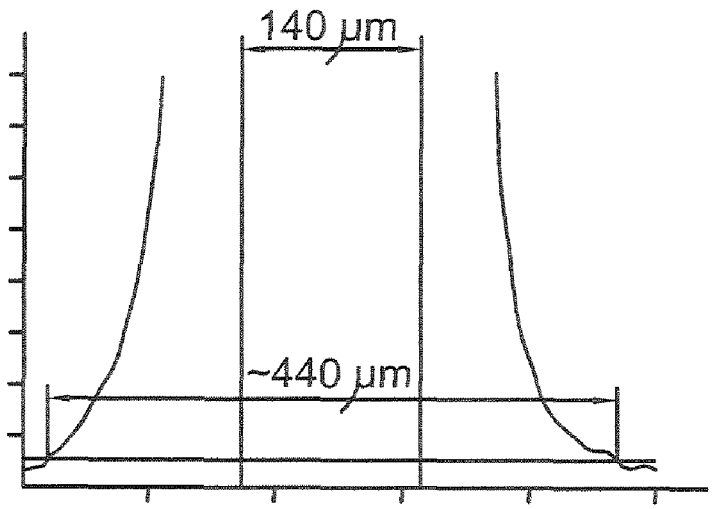

FIG. 10 illustrates a sectional view of a component according to the invention, inserted into a substrate, FIG. 11 illustrates a sectional view of a component according to the invention, inserted into a substrate, with contacts crossing the substrate, FIG. 12 illustrates a sectional view of a component according to the invention, inserted into a substrate, with contacts which do not completely cross the substrate, FIG. 13 illustrates a sectional view of a component according to the invention, inserted into a substrate in which supporting planes have been made, FIG. 14 illustrates a sectional view of a component according to the invention, with supporting planes, inserted into a substrate in which supporting planes have been made, FIG. 15 is an exemplary image obtained during a hybridization experiment of a DNA component by a HRP-coupled oligonucleotide, FIGS. 16A and 16B illustrate the results obtained during an experiment for measuring molecular diffusion before emission of photons, by means of a device according to the invention.

DETAILED DESCRIPTION OF PARTICULAR EMBODIMENTS

Figure 6:
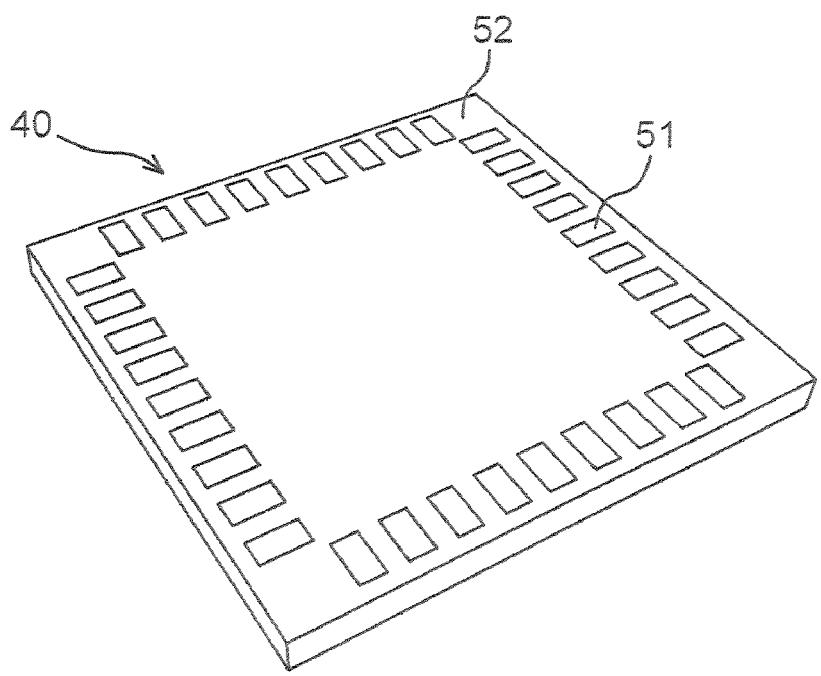
FIG. 6 illustrates the rear face of a component according to the invention.

An exemplary component which may be applied within the scope of the invention is illustrated in FIGS. 6 (rear face) and 7 (front face).

This is an APS (active pixel sensor) chip, i.e. including at the pixels 54, integrated electronic functions for reading and processing pixel information, with depassivated metal pads 51 for resuming contact on the rear face 52 (FIG. 6).

The front face 50 of the component groups together the functions of an optical and/or electrical detection component, for example in CMOS technology or any other technology based on a semiconductor (NMOS, BiCMOS . . . ). This may also be a component of a CCD detection array.

Examples of CMOS or MEMS or CCD technologies with resumption of contact on the rear face are given in the article of J. F. Kuhmann, entitled "Through Wafer Interconnects and Flip-Chip Bonding: A Toolbox for Advanced Hybrid Technologies for MEMS", EUROSENSORS XIII, 13th European conference on Solid-State Transducers, pp. 265-72 (The Hague 1999). ISBN: 90-76699-01-1.

The front face 50 may be passivated by a silicon oxide or silicon nitride layer. On the rear face 52 (FIG. 6), contact pads 51 appear, with which an electric connection may be made between this component and an external reader either via or not, an intermediate device (film, memory) on a read-out circuit.

An associated electronic processing circuit may also itself be made on the front face 50 and it fulfils various functions, such as for example: addressing and/or amplification, and/or analog or digital conversion . . . . Such a circuit is passivated.

Figure 8:
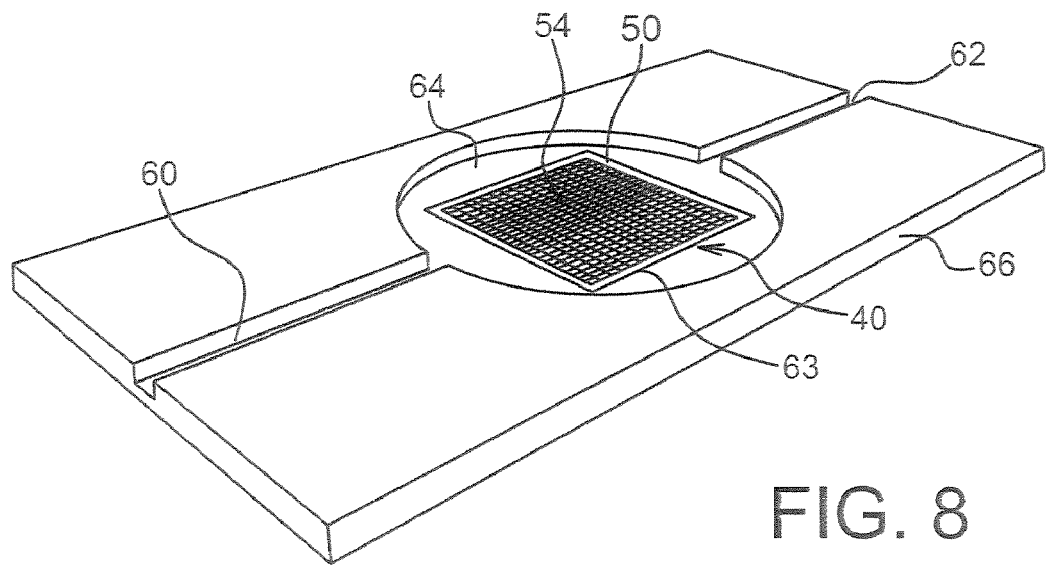
FIG. 8 illustrates an IAD according to the invention, in a front face view.
Figure 9:
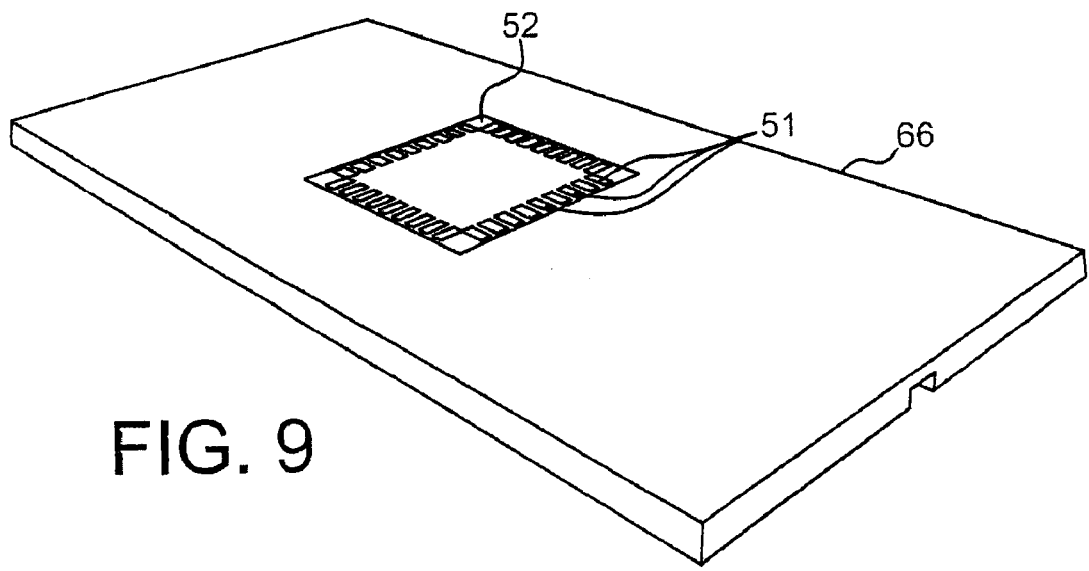
FIG. 9 illustrates an IAD according to the invention, in a rear face view.

An integrated analysis device according to the invention is illustrated in FIGS. 8 and 9.

FIG. 8 is a schematic view of an IAD in double face technology, in which a component 40 according to the invention is inserted into the fluidic portion, consisting of channels 60, 62 and of an aperture 64 made in a substrate 66.

Advantageously and as illustrated in FIG. 10, the component 40 in contact with the fluid through its front face 50, is assembled by the edge, in the bottom of the area 64 by means of an adhesive 63 moreover providing the seal of the fluidic portion. A memory film 65 may be positioned on the rear face (the side which is not exposed to the fluid), connected to the component by pads of contacts 68.

Still advantageously, the component is flush with the surface of the fluidic portion, as this is moreover apparent in FIG. 10: the front face 50 is at the same level as the face of the substrate 66 on which the fluid flows.

Fluidic flow does not thereby encounter any irregularity. No space is reserved for electric surface contacts.

The electric contacts 51 are directly accessible on the rear face (FIG. 9). They may for example be connected to a memory film.

Figure 1:
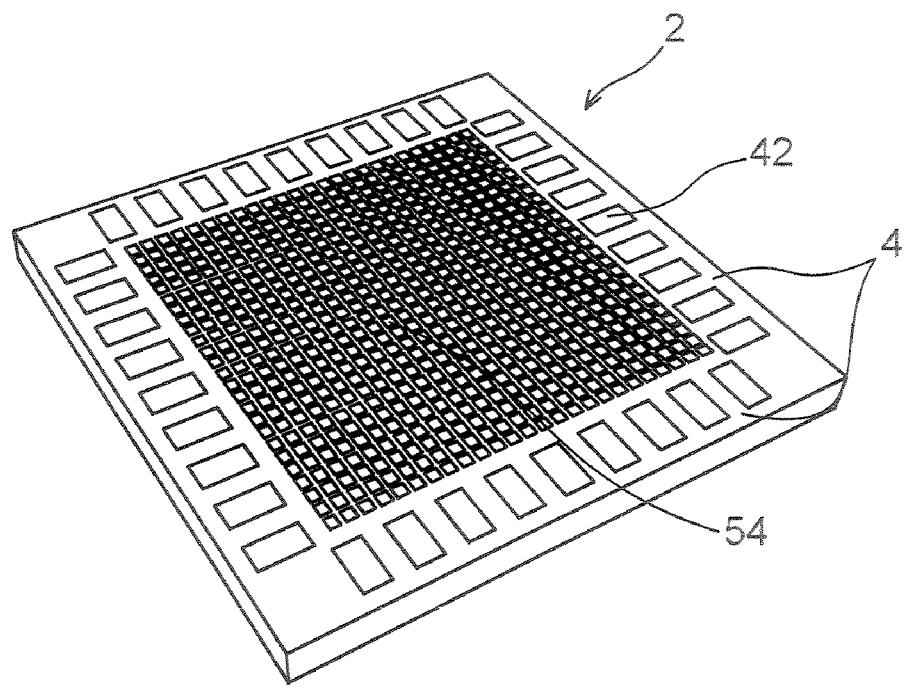
FIGS. 1-5 illustrate known devices.
Figure 2:
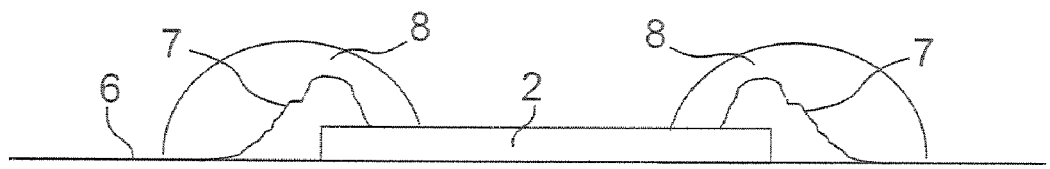
Figure 3:
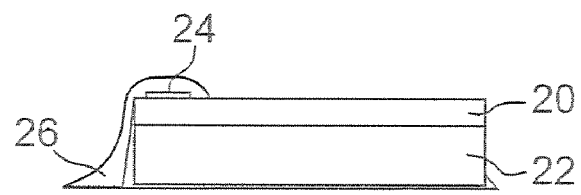

The electrical connections are made through the component 40, without any accessible connections on the front face 50 as in FIG. 1. Now, it is on this front face that the fluids to be analyzed will flow.

Two exemplary embodiments of such a device are given in FIGS. 11 and 12.

On these figures, reference 40 always designates the detection component used.

It is connected to contact pads 70-73, through contacts 80-83 which either completely cross the whole substrate 66 (FIG. 11) or not (FIG. 12). A passivation layer 87, 97 covers the detection surface 50. The other numerical references correspond to the components already explained earlier.

In the embodiment of FIG. 11, the contacts 80, 81 are, themselves, also on the front face, covered with a passivation layer 87. This structure further applies resumptions of contact 85, 89, between the contacts 80, 81 and the component, resumptions also located under the passivation layer.

With the embodiment of FIG. 12, it is possible to use a component with a larger detection surface 50.

The interconnection material may be in gold or in a titanium-gold alloy, or in nickel . . . etc.

With such a device, it is no longer necessary to take into account the metal nature of the pads 54 since, on the front face 50 of the component, one only has access to the passivation layer, for example in silicon nitride or in silicon dioxide, of the array of pixels and of the associated electronic processing circuit.

All the functionalization chemistries operating on a microscope slide may be contemplated on the passivation layer.

From a fluidic point of view, the surface 50 of the component, when it is flush with the fluidic portion, does not have any irregularity caused by resuming electrical contact and its associated passivation. This does not require any complementary study or development with regard to fluidic flows. The component may nevertheless, if desired, jut out into the fluidic chamber.

Figure 4:
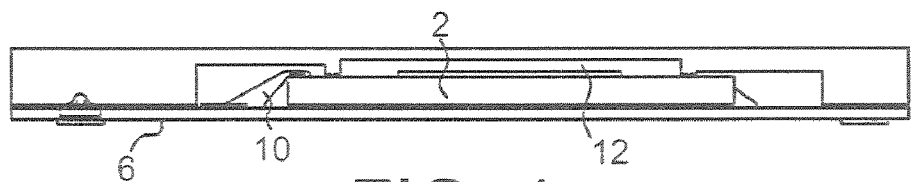
Figure 5:
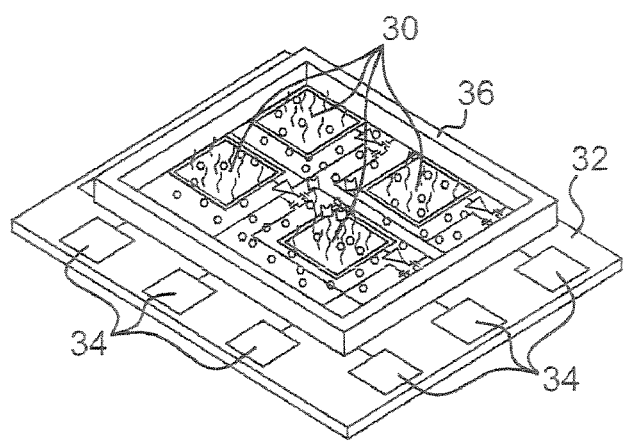
Figure 7:
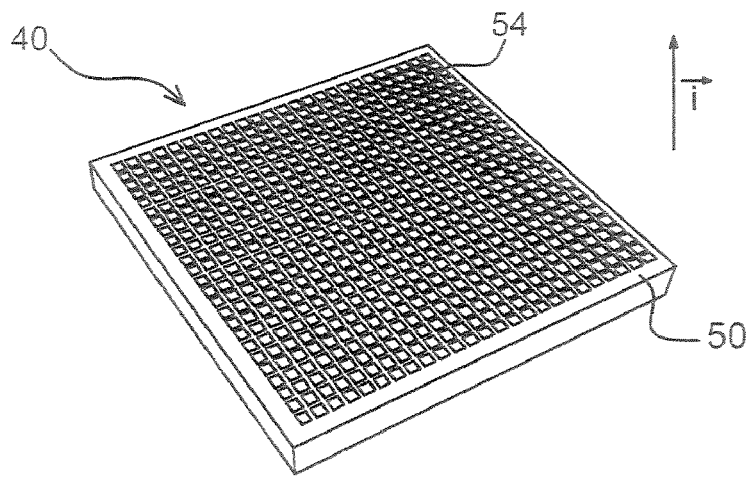
FIG. 7 illustrates the front face of a component according to the invention.

From the point of view of the assemblies, in the direction perpendicular to the main plane of the component (direction i of FIG. 7), a badly defined area for resuming contacts (as in FIG. 4) and their passivations are no longer reserved. The assembly may for example be achieved by a seal gasket between the fluidic portion of the sector and the edge of the detection component.

By means of this technology, methods for assembling a detection component in a biochip may be obtained much more simply than in the prior art.

In particular, as illustrated in FIGS. 13 and 14, supporting planes 166 may be made in the substrate 66 in which the fluidic portion 64 is made (FIGS. 13 and 14) and/or supporting planes 140 defined on the perimeter of the component (FIG. 14), with which assembling the detection chip may be facilitated in the fluidic portion of the biological analysis device.

Taking into account the one-way use which is contemplated for this type of IAD, it is moreover possible to achieve resumption of the electric contacts by an external <<reader>>, of the chip card reader type, directly in contact with the pads 54, on the rear face of the chip, and not via a memory film with which the contacts may be transferred. The dimension of these pads may be adapted in order to facilitate resumption of the contacts with standard tools.

The entire surface of the rear face 52 of the component is available for this purpose.

As a general rule, the active surface of the component is larger than the surface required for resuming the electric contacts, there is therefore a sufficient surface area on the rear face 52 of the component for making the whole of the electric contacts and even larger electric contact pads, compatible with the final reader, such as those conventionally used for resuming contact on a chip card.

By suppressing the memory film, it is possible to suppress the stresses related to the use of this film (alignment, mechanical strength, heat strength). It facilitates the assembling of the biological analysis device.

A heating resistor may be provided on the rear face of the component in order to control the temperature at the fluidic chamber. Advantageously, it may be made with the same technology as the one used for making the contact pads. Alternatively, an external heating resistor may be used (integral with the reader, for example); by suppressing the memory film, a direct thermal contact with the component will be possible in this case, providing better control of the temperature at the fluidic chamber.

According to another aspect, it is possible to considerably increase the surface of the connection pads, considering the available surface on the rear face 52 of the component. With this, the connector technology stresses (alignment, mechanical strength, temperature strength . . . ).

The front face of a component according to the invention may be functionalized by biological probes (DNA, or protein, or sugar), and then used as an integrated biological analysis device. The electrical functionalities of the component may be tested at any moment before or after functionalization via rear face contact pads.

Thus, a DNA, protein or other ligand biochip may be read in an integrated way, as described in document <<Opto-electronic DNA chip: high performance chip reading with an all-electric interface, F. Mallard et al>>.

Any detection of molecules and notably of organic molecules, may also be applied, as described in documents U.S. Pat. No. 5,653,939 or U.S. Pat. No. 6,325,977, and this thanks to optical detection means, for example by fluorescence or bioluminescence or chemiluminescence, or to electrical means.

Six examples will now be given. In these examples, the term <<component>> means a component according to the present invention:

EXAMPLE 1

Functionalization of an Array of Photodetectors

The surface of the APS component used is covered with a silicon nitride passivation layer. Captured oligonucleotides are grafted on the surface of the APS via a silane bearing reactive groups.

1-1: Creation of SiOH Groups on the Surface of the APS:

The components are subject to an $O_2$ plasma of 500 W for 1 minute. Alternatively, the components are incubated for two hours in an NaOH, $H_2O$, ethanol mixture in mass proportions 1:3:4 (<<Brown>> treatment) and then thoroughly washed with water and dried under nitrogen flow.

1-2: Silanization:

The components are incubated for 24 hours at room temperature in an absolute ethanol+10% 3-aminopropyltriethoxysilane mixture. They are then rinsed several times with ethanol, including once with sonication for 5 minutes, and then dried under nitrogen flow and incubated for 3 hours 110° C. (annealing).

1-3: Pre-Activation:

The components are immersed in a solution of KOH (7.5% by mass in water) and then thoroughly rinsed with water. This step provides regeneration of the $NH_2$ groups of the silanes, which may have been protonated ($NH_3^+$, less reactive in the following step).

1-4: Activation:

The components are immersed for 90 minutes at room temperature in an aqueous 20% glutaraldehyde solution. Next, they are thoroughly rinsed with water and dried under nitrogen flow.

1-5: Binding the Captured Oligonucleotides:

A capture probe bearing an amine group is then diluted to finally 10 µM in the deposit buffer (300 mM $Na_2HPO_3$, pH 7.8, 10% glycerol), and then deposited on the surface of the component by means of a Karl Züss stopper robot provided with a piezoelectric needle. The deposit volume of the order of 300 pl and the diameter of the drop is about 140 µm.

In Example 2, the capture probe used is the 20mer, (5') AATAGTACTTTCCTGATTCC(3')-$NH_2$.

The deposits remain in contact with the surface of the components overnight, and then the components are washed three times with the deposit buffer before post-immobilization treatment.

1-6: Post-Immobilisation Treatment:

The components are incubated for 1 hour at room temperature and without stirring, in an aqueous 90 mM $NaBH_4$ solution, rinsed with water for 5 minutes, in a 0.2% SDS solution for 5 minutes, again rinsed with water for 5 minutes, and then dried under nitrogen flow.

EXAMPLE 2

Experiment for Hybridizing an DNA Chip by a HRP-Coupled Oligonucleotide

On a component functionalized according to the procedure described in Example 1, 10 nM of HRP-coupled detection oligonucleotide complementary to the detection probe, is hybridized as a drop at 37° C. for 30 minutes (here: (5') GGAATCAGGAAAGTACTATT(3')-HRP) in a hybridization buffer (100 mM Tris, pH 8.0, 1 mM EDTA, 1M NaCl, 0.05% Triton X-100).

The surface of the component is then washed three times with a hybridization buffer, and then the components are mounted on their read-out device (test kit for VV5501 chips of STMicroelectronics). The Pierce ELISA Femto Maximum Sensitivity chemiluminescence substrate is deposited as a drop on the surface, the component is placed in darkness, and then 64 non-saturated images of the luminescent spots are acquired.

After acquisition of the signal, the luminescence is quenched by adding Javel water (fast oxidation of all the present luminols), and then 64 images are acquired with the same camera adjustment (acquisition of black images).

The final image of the spots is the difference between the averages of the 64 signal images and of the 64 black images.

FIG. 15 is a final image example. Five lines of spots (no spot spacings: 200 µm, no line spacings: 400 µm, diameter of the spots: ~140 µm) are visible.

EXAMPLE 3

Measurement of Molecular Diffusion Before Emission of Photons

The detail of the reaction mechanism of the HRP/luminol pair demonstrates that the photon-emitting species, like the species from which they originate, freely diffuse in solution (only the first step of the reaction chain depends on HRP). The size of a spot observed in chemiluminescence should therefore be larger than its actual size. This has an influence on the maximum density of biological sites which may be put on the array of photodetectors.

An attempt was made to quantify the diffusion distance of the photon-emitting species: on an image similar to the one shown in FIG. 15 (non-saturated image, a saturating surface density of the detection probe for the signal), the intensity profile of a spot was plotted.

The difference between the average diameter of the spot (estimated by its peak's width at half maximum) and the diffusion diameter of the spot (the area on the spot, where light intensity is larger than one thousandth of the maximum intensity) was thus able to be measured.

FIGS. 16A and 16B illustrate the obtained result: the distances along the lines are plotted in abscissae and the grey level light intensities in ordinates. FIG. 16B illustrates an enlargement of the base of the peak for graphically measuring the apparent diameter of the spot, at ¹⁄₁₀₀₀ of the maximum intensity.

In the case illustrated in FIGS. 16A and 16B, the <<real>> size of the spot is 140 µm whereas the diffusive spot has a diameter of 440 µm.

EXAMPLE 4

Complete Analysis of a Biological Sample

This example relates to the general course of the treatment of a sample and hybridization.

A component is obtained according to any of the methods described in Example 1.

A biological sample is treated in order to extract and purify the nucleic acids of interest, and then to amplify them according to state-of-the-art techniques, for example the method described in Troesch et al., Journal of Clinical Biology, 1999, 37, 49-55.

The amplified nucleic acids are then marked with biotin on the phosphate groups of DNA and cleaved into small fragments according to the method described in <<Procédé de marquage et de fragmentation d'ADN>>, (method for marking and fragmenting DNA), Patent Application FR-2 824 335. These marked and cleaved nucleic acids are then purified according to standard state-of-the-art techniques, in order to remove the excess of marker (see for example Monnot et al., Nucleos. Nucleot. & Nucleic acids, 2001, 20(4-7), 1177-1179).

The amplified, marked, cleaved nucleic acids are then hybridized on the component for 30 minutes according to the aforementioned techniques of the art (Troesch et al. 1999). The hybridized component is then washed in order to remove the nucleic acids which are not specifically coupled to the component, always according to the methods of the art.

A streptavidin/HRP conjugate is then deposited on the component at a concentration from 10 to 20 nM for 5 to 15 minutes, and then the component is washed again in order to remove the conjugates which are not specifically complexed to nucleic acids marked with biotin.

The Pierce ELISA Femto Maximum Sensitivity chemiluminescence substrate is then introduced there onto the chip, and the treatment described in Example 2 above is then followed.

EXAMPLE 5

Functionalization of a Photodetector Array Via a Photochemical Route

Example 1 above shows a functionalization of the component by spotting.

However, it is possible to use other functionalization methods presently in effect in the field of biochip type components.

In particular, a preferential method for making the component is to use a functionalization method addressed by light, as practised by Affymetrix (cf. Fodor et al. Science, 1991, 251, 767-773, or further Pease et al., Proc. Nat. Acad. Sci.

USA, 1994, 91, 5022-5026). This method derived from methods of microelectronics, uses a succession of insolations (UVA) and of chemical reactions on a glass or silica wafer in order to make a component of peptides or oligonucleotides.

The methods for making arrays of photodetectors also themselves use techniques of microelectronics, in particular thin layer deposition, insolation (UVA) end etching steps, on a silicon substrate.

Thus, an industrial manufacturing method may be the following:
- making substrates bearing arrays of APS photodetectors, according to the desired specifications (size and arrangement of the pixels, nature of the passivation layer, firmware integrated to the chip, . . . ),
- functionalizing the substrates,
- cutting them out and packaging them.

EXAMPLE 6

A Fluorescence Case

The functionalized detection face is excited by a beam with a suitable wavelength. A fluorescence beam with a different wavelength is re-emitted and read at the detection face.

Advantageously in this case, provision is made for adding on the optical detection face, a wavelength filter which is reflective at the excitation wavelength and transparent at the fluorescence wavelength.

The invention claimed is:

1. A biological analysis device comprising:
a substrate including
a fluidic chamber formed as an aperture in the substrate, and
a plurality of channels formed in the substrate to circulate a fluid to be analyzed through the fluidic chamber; and
a semiconductor device mounted in a cut-out at a bottom of the fluidic chamber, the cut-out extending through the substrate, the semiconductor device including
a front face disposed in the fluidic chamber, the front face having an optical detector in contact with the fluid to be analyzed in the fluidic chamber, the front face being flush with a surface of the bottom of the fluidic chamber,
a passivation layer to cover the front face, and
a rear face disposed outside the fluidic chamber opposite the front face, the rear face having a plurality of electrical contact pads to electrically connect the optical detector to an external device.

2. The device according to claim 1, the front face being functionalized by biological and/or chemical probes.

3. The device according to claim 1, wherein the optical detector is a fluorescence detector.

4. The device according to claim 3, further including a wavelength filter disposed on the front face and configured to reflect an excitation wavelength, the wavelength filter being transparent to fluorescent wavelengths.

5. The device according to claim 1, the optical detector being bioluminescence or chemiluminescence detector.

6. The device according to claim 1, comprising biological probes marked with an enzyme capable of emitting a photon upon contact with a specific molecule of a fluid to be analyzed.

7. The device according to claim 1, wherein the front face of the semiconductor substrate is flush with the fluidic chamber at a flow surface of a fluid.

8. The device according to claim 1, wherein the optical detector comprise an array of detection pixels.

9. The device according to claim 8, comprising electronic processing circuits at each pixel and/or the array.

10. The device according to claim 1, wherein the passivation layer covers the optical detector of the front face.

11. The device according to claim 10, wherein the passivation layer is in silicon nitride or in silicon oxide.

12. The device according to claim 1, further comprising a seal to seal the fluidic chamber in an area in proximity to the optical detection means or in an area for inserting optical detection means into the chamber.

13. The device according to claim 1, wherein the perimeter of the device comprises supporting planes.

14. The device according to claim 13, wherein the fluidic chamber comprises supporting planes.

15. The device according to claim 1, further comprising a heating resistor on a side of the rear face.

16. The device according to claim 1, further comprising a memory film positioned in contact with the pads on the rear face of the detection means.

17. The device according to claim 1, wherein the electrical contact pads are directly connected to an external reader.

18. A biological analysis device comprising:
means for circulating a fluid to be analyzed, comprising a fluidic chamber,
means for detecting molecules using optical fluorescence, the means for detecting being arranged on a front face of a semiconductor device installed in a cut-out at a bottom of the fluidic chamber, the cut-out extending through the bottom of the fluidic chamber, the front surface of the semiconductor being flush with a surface of the bottom of the fluidic chamber, the means for detecting being functionalized by biological and/or chemical probes, the means for detecting being in contact with the fluid to be analyzed in the fluidic chamber, electrical contact pads being located on a rear face, opposite the front face, of the semiconductor device to connect to an external device;
means for passivating the front surface of the semiconductor; and
means for reflecting an excitation wavelength, the means for reflecting being transparent to fluorescent wavelengths, the means for reflecting being disposed on the front face of the semiconductor device.

19. A biological analysis device comprising:
means for circulating a fluid to be analyzed, comprising a fluidic chamber;
means for optically detecting bioluminescence or chemiluminescence, the means for optically detecting being disposed on a front face of a semiconductor device installed in a cut-out formed through a bottom of the fluidic chamber, the means for optically detecting being functionalized by biological and/or chemical probes, the front surface of the semiconductor being flush with a surface of the fluidic chamber, the means for optically detecting being in contact with the fluid to be analyzed in the fluidic chamber, a rear face, opposite the front face, of the semiconductor device including electrical contact pads to connect to an external device; and
means for passivating the front surface of the semiconductor.

20. A method for carrying out biological analyses comprising contacting a biological sample with the device of claim 1 and analyzing results by the detection means of the device of claim 1.

21. The device according to claim 17, wherein the contact pads protrude from a rear surface of the substrate.

* * * * *